United States Patent [19]

Nass et al.

[11] Patent Number: 5,336,695
[45] Date of Patent: Aug. 9, 1994

[54] HYDROPHILIC FOAMS AND PROCESSES FOR THEIR MANUFACTURE

[75] Inventors: Martina Nass; Heidi Sacker, both of Hamburg, Fed. Rep. of Germany

[73] Assignee: Beiersdorf Aktiengesellschaft, Hamburg, Fed. Rep. of Germany

[21] Appl. No.: 129,068

[22] PCT Filed: Mar. 6, 1992

[86] PCT No.: PCT/DE92/00192

§ 371 Date: Oct. 4, 1993

§ 102(e) Date: Oct. 4, 1993

[87] PCT Pub. No.: WO92/17518

PCT Pub. Date: Oct. 15, 1992

[30] Foreign Application Priority Data

Apr. 5, 1991 [DE] Fed. Rep. of Germany ....... 4111098

[51] Int. Cl.$^5$ .............................................. C08G 18/30
[52] U.S. Cl. .................... 521/109.1; 521/99; 521/137; 521/159; 521/174; 521/905; 528/59; 528/76; 528/77; 428/304.4; 428/319.3; 428/423.1
[58] Field of Search ....... 521/109.1, 99, 137, 521/159, 174, 905; 528/59, 76, 77; 428/304.4, 319.3, 423.1

[56] References Cited

U.S. PATENT DOCUMENTS 3,978,855 9/1976 McRae et al. ................. 528/45

FOREIGN PATENT DOCUMENTS 0196364 10/1986 European Pat. Off. .
0271292 6/1988 European Pat. Off. .
0299122 1/1989 European Pat. Off. .

*Primary Examiner*—Maurice J. Welsh
*Attorney, Agent, or Firm*—Sprung Horn Kramer & Woods

[57] ABSTRACT

Hydrophilic foams based on a polyurethane gel material which can be obtained from
  one or more polyether-polyols selected from the group comprising substances formed by the addition of propylene oxide and optionally ethylene oxide on to conventional starter molecules,
  one or more diisocyanates,
  one or more superabsorbers,
  one or more accelerators selected from the group comprising conventional accelerators for polyurethanes,
  water, and optionally
  conventional auxiliary substances and/or additives.

14 Claims, No Drawings

HYDROPHILIC FOAMS AND PROCESSES FOR THEIR MANUFACTURE

DESCRIPTION

The present invention relates to hydrogel foams, especially those for medicinal applications, and to processes for their manufacture.

Hydrogels are natural or synthetic macromolecular substances whose high content of hydrophilic groups makes them capable of binding water by absorption. The water absorption capacity of many hydrogels is several times the intrinsic weight of the anhydrous substance.

Hydrogels are used in a variety of forms in medicine. They are particularly suitable in the care of wounds; they can protect wounds from drying out,
absorb the exudation of wounds,
serve as a matrix for all kinds of active substances,
serve as a basis for colonisation with autologous or heterologous skin cells.

Hydrogels can be used inter alia in the form of foams. Foams for the care of skin wounds or surgical wounds are known per se, the principal foams used in this case being polyurethane foams or collagen foams.

However, the hydrogels of the state of the art have various disadvantages:

Due to their hydrophilicity, most of the substances in question are water-soluble. This is usually undesirable because such products are not dimensionally stable. Moreover, such products dissolve in undesirable manner at the site of use and are then no longer available for the intended purpose.

Other products are distinguished by a high degree of polymer crosslinking. Although this avoids some of the disadvantages of the above-mentioned class of substances, the swelling capacity of these substances is substantially reduced or lost. Furthermore, all the synthetic crosslinking agents used here are more or less toxic.

Self-adhesive gel foams are also known per se. Although these can generally be bonded very well to the skin, most of them have the disadvantage that their water absorption and release capacity are greatly reduced.

European patent application A-0 097 846 describes wound treatment compositions based on hydrogels. Here, gelatin in solid form, as powder, flakes or sheet, is reacted in a two-phase reaction with crosslinking agents such as formaldehyde, glyoxal, glutaric acid dialdehyde, dicarboxylic acid chlorides and/or diisocyanates.

The crosslinking agent acts in this case on the swollen undissolved gelatin. This process and the products obtained therefrom suffer from considerable disadvantages because the crosslinking agents used can cause appreciable cell damage.

In addition, the process cannot easily be reproduced, if at all. The crosslinking depends not only on the concentration of the crosslinking agents used, but also on parameters such as temperature and reaction time of the reactants. Furthermore, the effective surface area and the average molecular weight of the commercially available types of gelatin are subject to marked variations, so it is also difficult to predict the properties of the crosslinked hydrogel.

European patent application A-0 097 846 further describes a composite material made of hydrogels based on polyvinyl alcohol. The crosslinking agent used is formaldehyde, which, as mentioned at the outset, is physiologically harmful.

Foams made of polyvinyl alcohol or collagen are also known and in common use. However, as their matrix substances have the disadvantages described above, their suitability for wound care is at best limited.

Furthermore, hydrophilic foams made of polyurethane gels are known. PCT patent application WO-88/01878 describes self-adhesive polyurethane foams and polyurethane foam gels which inter alia can contain methacrylates.

Polyurethane gels based on a polyurethane matrix and higher-molecular polyols are also described in European patent application B-0 057 839. Self-adhesive two-dimensional structures made of polyurethane gels are known from European patent application B-0 147 588. However, the polyurethane gels disclosed in these last two documents are anhydrous and unfoamed.

The object of the invention was therefore to develop hydrogel foams which do not have the disadvantages of the state of the art and are suitable as wound care compositions. Moreover, it should be possible to manufacture the foams economically by reproducible processes.

Surprisingly, it has been found that the disadvantages of the state of the art are mitigated by hydrophilic foams based on a polyurethane gel material which can be obtained from one or more polyether-polyols selected from the group comprising substances formed by the addition of propylene oxide and optionally ethylene oxide on to conventional starter molecules,
one or more diisocyanates,
one or more superabsorbers,
one or more accelerators selected from the group comprising conventional accelerators for polyurethanes,
water, and optionally
conventional auxiliary substances and/or additives.

It is this finding which enables the above-stated objects to be achieved.

The hydrophilic foams according to the invention are especially distinguished by an extremely high water absorption capacity. For example, the water absorption capacity can be one hundred times the intrinsic dry weight of the hydrogel foams according to the invention.

The starter molecules for the polyether-polyols are preferably pentaerythritol, sorbitol, trimethylolpropane or ethylenediamine.

Particularly advantageously, the polyetherpolyols used are those also described in European patent applications B-0 057 839 and B-0 147 588.

The diisocyanates are selected either from the group comprising unmodified aromatic or aliphatic diisocyanates, a very advantageous example being 4,4'diisocyanatodiphenylmethane, or from modified products formed by prepolymerisation with polyols or polyetherpolyols. 4,4'-Diisocyanatodiphenylmethane liquefied by prepolymerisation with tripropylene glycol has proved a very favourable example. Particularly advantageously, the diisocyanates used are those also described in European patent applications B-0 057 839 and B-0 147 588.

The accelerators are particularly advantageously selected from the group comprising organic acids, especially p-toluenesulphonic acid and n-butylphosphoric acid, organotin compounds, including their salts with organic and inorganic acids, especially tin naphthenate, tin benzoate, dibutyltin dioctoate, dibutyltin dilaurate, tin(II) ethylhexanoate and dibutyltin diacetate, iron salts of higher fatty acids, especially iron stearate, isophoronediamine, methylenedianiline and imidazoles, and tertiary a/nines, especially trialkyleanines, the alkyl radicals advantageously having 2-6 carbon atoms.

In terms of the present invention, superabsorbers are understood in particular as meaning substances which have a high absorption capacity for liquids, especially water, and retain the absorbed liquids even under load, in contrast to cellulose fibres, for example.

The superabsorbers are advantageously selected from the group comprising the sodium salts of polyacrylates. Particularly advantageously, the chosen superabsorbers are those which are non-crosslinked or only weakly crosslinked and can be selected from all the conventional commercial products of this type. Particularly suitable products are those disclosed in German patent application A-37 13 601, but other conventional superabsorbers, e.g. selected from the group comprising carboxymethyl cellulose derivatives, karaya, cellulose, pectin, polyvinyl alcohol, polyvinylpyrrolidone or gelatin, are also advantageous.

The auxiliary substances and additives can also be selected from the conventional classes of substances. The following are particularly advantageous: dyestuffs, pigments, light stabilisers, preservatives, fragrances, substances having an antimicrobial action, other active substances such as, for example, those having a cooling action (e.g. menthol) or those which promote circulation or produce a feeling of warmth, and so on.

Particularly advantageously, the hydrogel foams according to the invention can be applied by processes known per se to two-dimensional bases, e.g. woven fabrics, knitted fabrics, non-woven fabrics, films or the like.

The invention further relates to a process for the manufacture of hydrophilic foams, characterised in that
one or more polyether-polyols selected from the group comprising substances formed by the addition of propylene oxide and optionally ethylene oxide on to conventional starter molecules,
one or more diisocyanates,
one or more superabsorbers,
one or more accelerators selected from the group comprising conventional accelerators for polyurethanes, and
water
are combined and mixed together and, if appropriate, additionally foamed, mechanically and/or by the introduction of gas, and, if appropriate,
cast or spread out to form two-dimensional objects, or
applied to two-dimensional bases, or
cast to form space-filling objects.

The polyether-polyols can for example be commercial products such as Levagel VP SN 100. Commercial products such as Desmodur PF, Desmodur N 100, IPDI and Desmodur W have proved suitable as diisocyanates. Sodium polyacrylate, especially the sodium polyacrylate resin known as Favor 922-SK, has shown itself to be advantageous as a superabsorber.

Desmorapid Z/SN and Desmorapid SO are advantageous commercial products as dibutyltin dilaurate and tin(II) ethylhexanoate accelerators, respectively.

Advantageously, the foams according to the invention can be obtained from
20-95% by weight of polyether-polyol
1-60% by weight of diisocyanate
5-60% by weight of superabsorber
0.001-1.00% by weight of accelerator
0.01-20% by weight of water Particularly advantageously, the foams according to the invention can be obtained from
20-95% by weight of polyether-polyol
1-60% by weight of diisocyanate
5-60% by weight of sodium polyacrylate
0.001-1.00% by weight of accelerator
0.01-20% by weight of water Preferably, the foams according to the invention can be obtained from
50-70% by weight of polyether-polyol
5-25% by weight of diisocyanate
15-35% by weight of superabsorber
0.05-1.00% by weight of accelerator
0.1-10% by weight of water Particularly preferably, the foams according to the invention can be obtained from
50-70% by weight of polyether-polyol
5-25% by weight of diisocyanate
15-35% by weight of sodium polyacrylate
0.05-1.00% by weight of accelerator
0.1-10% by weight of water The ratios of polyether-polyol to isocyanate are advantageously chosen to be (5-15):1, especially about (8-12):1.

It is possible to control the adhesive properties of the foams according to the invention through the ratio of polyol to isocyanate. Thus the foams obtained for a polyol-to-isocyanate ratio of about 10:1 are weakly adhesive, if at all, and strongly cohesive. The adhesive strength increases if the ratio becomes greater than about 10:1. If the ratio decreases, the cohesive strength decreases as well.

After a pot life of advantageously about 2-30 minutes, the foams can be cast or spread out to form two-dimensional structures. For thicknesses of 0.10 mm to at least 15 mm can be achieved in this way without difficulty. It is also possible and advantageous, however, to produce from the hydrogel foams according to the invention objects which are not two-dimensional but distinctly space-filling, for example by means of conventional casting processes.

The foams formed are open-pore foams if then the foam raw material is cast and coated on to an adhesive base, i.e. a base whose surface has an adhesive-repellent nature. In such a case it is not necessary to convert them to open-pore foams by cutting.

Although it is possible, as already mentioned, to control the adhesive properties of the foes according to the invention so that the resulting foams or the bases coated therewith can be self-adhesive, they can advantageously also be coated on one or both of their large surfaces with a conventional self-adhesive material.

The finished foam, preferably the above-described two-dimensional structures, but advantageously also the bases coated with hydrogel foam, can be used for example to care for surface wounds or surgical wounds.

One particular surprising advantage of the foams according to the invention is that they can be removed from human tissue, and especially wounds, without leaving the slightest residue and without the already damaged tissue suffering any further damage.

A particularly advantageous area of application is therefore the care of deep wounds, especially because the foams according to the invention can adhere to one another.

Several thin layers of foam, which individually are very easy to cut into suitable shapes, can thus be stacked on top of one another in or on the wound without the need for other bonding aids. This enables the same effect to be achieved as with one thick layer of foam.

The cohesive property of some of the foams according to the invention also makes them suitable for use as cohesive bandages. These are to be understood as meaning bandages which adhere to themselves but not to human tissue.

The Examples which follow will illustrate the invention, although it is not intended to restrict the invention to these Examples.

EXAMPLE 1

| | |
|---|---|
| Levagel VP SN 100 | 61% by weight |
| Favor 922 SK | 24% by weight |
| Dibutyltin dilaurate | 0.1% by weight |
| Water | 4.9% by weight |
| Desmodur PF | 7% by weight |

EXAMPLE 2

| | |
|---|---|
| Levagel VP SN 100 | 69% by weight |
| Favor 922 SK | 18% by weight |
| Dibutyltin dilaurate | 0.1% by weight |
| Water | 2.9% by weight |
| Desmodur PF | 10% by weight |

EXAMPLES 3

| | |
|---|---|
| Levagel VP SN 100 | 58% by weight |
| Favor 922 SK | 33% by weight |
| Dibutyltin dilaurate | 0.1% by weight |
| Water | 2.9% by weight |
| Desmodur PF | 6% by weight |

The components of the compositions according to Examples 1-3 are combined all at once and mixed together. The pot life, i.e. the processing time of the mixture while still fluid, is 1.5-10 minutes. The foams can be spread out and processed further.

We claim:

1. Hydrophilic foams based on a polyurethane gel material which can be obtained from
   one or more polyether-polyols selected from the group consisting of substances formed by the addition of propylene oxide and optionally ethylene oxide on to starter molecules,
   said starter molecules being selected from the group consisting of pentaerythritol, sorbitol, trimethylolpropane or ethylenediamine,
   one or more diisocyanates,
   one or more superabsorbers,
   said superabsorbers being selected from the group consisting of sodium salts of polyacrylates, or the group consisting of carboxymethyl cellulose derivatives, karaya, cellulose, pectin, polyvinyl alcohol, polyvinylpyrrolidone and gelatin,
   one or more accelerators selected from the group consisting of conventional accelerators for polyurethanes,
   water, and optionally
   conventional auxiliary substances and/or additives.

2. Foams according to claim 1, characterised in that the diisocyanates are selected from the group consisting of unmodified aromatic or aliphatic diisocyanates, and modified products formed by prepolymerisation with polyols or polyether-polyols.

3. Foams according to claim 1, characterised in that the accelerators are selected from the group consisting of
   organic acids,
   organotin compounds and organic and inorganic salts thereof,
   iron salts of higher fatty acids,
   isophoronediamine, methylenedianiline and imidazoles, and
   tertiary amines,
   the alkyl radicals of which have 2-6 carbon atoms.

4. Foams according to claim 1, having the following composition:
   20-95% by weight of polyether-polyol
   1-60% by weight of diisocyanate
   5-60% by weight of superabsorber
   0.001-1.00% by weight of accelerator
   0.01-20% by weight of water 5. Foams according to claim 1, having the following composition:
   20-95% by weight of polyether-polyol
   1-60% by weight of diisocyanate
   5-60% by weight of sodium polyacrylate
   0.001-1.00% by weight of accelerator
   0.01-20% by weight of water 6. Foams according to claim 1, having the following composition:
   50-70% by weight of polyether-polyol
   5-25% by weight of diisocyanate
   15-35% by weight of superabsorber
   0.05-1.00% by weight of accelerator
   0.1-10% by weight of water 7. Foams according to claim 1, having the following composition:
   50-70% by weight of polyether-polyol
   5-25% by weight of diisocyanate
   15-35% by weight of sodium polyacrylate
   0.05-1.00% by weight of accelerator
   0.1-10% by weight of water 8. A process for the manufacture of self-adhesive hydrophilic foams according to claim 1 wherein
   one or more polyetherpolyols selected from the group consisting of substance formed by the addition of propylene oxide and optionally ethylene oxide on to starter molecules,
   said starter molecules being selected from the group consisting of pentaerythritol, sorbitol, trimethylolpropane or ethylenediamine,
   one or more diisocyanates,
   a superabsorber,
   said superabsorbers being selected from the group consisting of sodium salts of polyacrylates, or
   the group consisting of carboxymethyl cellulose derivatives, karaya, cellulose, pectin, polyvinyl alcohol, polyvinylpyrrolidone and gelatin, one or more accelerators selected from the group consisting of conventional accelerators for polyurethanes, and water are combined and mixed together and, if appropriate, additionally foamed, mechanically and/or by the introduction of gas, and, if appropriate, cast or spread out to form two-dimensional objects, or applied to two-dimensional bases, or cast to form space-filling objects.

9. Two-dimensional objects consisting of two-dimensional objects obtainable according to claim 8.

10. Use of two-dimensional objects according to claim 9 as cohesive bandages.

11. Two-dimensional objects consisting of two-dimensional bases coated with the hydrophilic foams of claim 1, said bases being selected from the group consisting of woven fabrics, knitted fabrics, non-woven fabrics and films.

12. Two-dimensional objects consisting of coated bases obtainable according to claim 8, said bases being selected from the group consisting of woven fabrics, knitted fabrics, non-woven fabrics and films.

13. A method for treating wounds which comprises applying thereto a foam in accordance with claim 1.

14. A method for treating wounds which comprises applying thereto a two dimensional object in accordance with claim 9.

* * * * *